United States Patent
Kling et al.

(10) Patent No.: US 10,049,318 B2
(45) Date of Patent: Aug. 14, 2018

(54) IN-SITU BALANCING OF PLATED POLYMERS

(71) Applicant: United Technologies Corporation, Hartford, CT (US)

(72) Inventors: Colin J. Kling, Newington, CT (US); Joseph Parkos, East Haddam, CT (US); Gary M. Lomasney, Glastonbury, CT (US); William Bogue, Hebron, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 269 days.

(21) Appl. No.: 14/903,915

(22) PCT Filed: Jul. 9, 2014

(86) PCT No.: PCT/US2014/045945
§ 371 (c)(1),
(2) Date: Jan. 8, 2016

(87) PCT Pub. No.: WO2015/026448
PCT Pub. Date: Feb. 26, 2015

(65) Prior Publication Data
US 2016/0145758 A1    May 26, 2016

Related U.S. Application Data

(60) Provisional application No. 61/844,030, filed on Jul. 9, 2013.

(51) Int. Cl.
C25D 5/06    (2006.01)
C25D 17/14   (2006.01)
(Continued)

(52) U.S. Cl.
CPC .... G06K 19/07749 (2013.01); B29C 37/0025 (2013.01); B29C 67/0062 (2013.01);
(Continued)

(58) Field of Classification Search
CPC .................................. C25D 5/06; C25D 17/14
(Continued)

(56) References Cited

U.S. PATENT DOCUMENTS 2,432,659 A * 12/1947 Criswell ................. G01M 1/30
118/301
3,909,584 A *  9/1975 Brienza .............. B23K 26/0823
219/121.6
(Continued)

FOREIGN PATENT DOCUMENTS

EP    0487854 B1    6/1992
EP    1736566 A1    12/2006
(Continued)

OTHER PUBLICATIONS

English Abstract for Japanese Application No. JP2011017056A; Filing date: Jan. 27, 2011; 1 pg.
(Continued)

Primary Examiner — Bryan D. Ripa
(74) Attorney, Agent, or Firm — Cantor Colburn LLP

(57) ABSTRACT

A method for balancing a rotatable component is disclosed This method comprises and then plating the component to deposit a metal layer onto the component until the component is balanced. In addition, and alternative method for balancing a rotatable component is disclosed. This method comprises attaching a balancing weight to the rotatable component and rotating the component. This is followed by plating the component and the balancing weight to deposit a metal layer onto the balancing weight and the component until the component is balanced.

17 Claims, 6 Drawing Sheets

(51) Int. Cl.

| | | |
|---|---|---|
| G06K 19/077 | (2006.01) | |
| G01N 3/08 | (2006.01) | |
| C23C 18/16 | (2006.01) | |
| C23C 28/02 | (2006.01) | |
| C23C 18/22 | (2006.01) | |
| C25D 1/02 | (2006.01) | |
| C25D 1/20 | (2006.01) | |
| C25D 7/04 | (2006.01) | |
| C25D 3/02 | (2006.01) | |
| C25D 5/56 | (2006.01) | |
| C25D 7/00 | (2006.01) | |
| C25D 9/02 | (2006.01) | |
| C25D 17/12 | (2006.01) | |
| B29C 37/00 | (2006.01) | |
| B29C 67/00 | (2017.01) | |
| C23C 18/30 | (2006.01) | |
| C23C 18/32 | (2006.01) | |
| C25D 1/00 | (2006.01) | |
| G01B 7/16 | (2006.01) | |
| G01D 5/12 | (2006.01) | |
| B29C 70/42 | (2006.01) | |
| B29C 70/54 | (2006.01) | |
| B32B 27/08 | (2006.01) | |
| C25D 5/54 | (2006.01) | |
| B32B 27/28 | (2006.01) | |
| B33Y 10/00 | (2015.01) | |
| B29K 79/00 | (2006.01) | |
| B29K 105/00 | (2006.01) | |
| B29K 105/12 | (2006.01) | |
| B29K 307/04 | (2006.01) | |
| B29K 309/08 | (2006.01) | |
| B29L 9/00 | (2006.01) | |
| B29L 31/08 | (2006.01) | |
| B33Y 70/00 | (2015.01) | |
| B33Y 80/00 | (2015.01) | |

(52) U.S. Cl.
CPC .......... *B29C 67/0077* (2013.01); *B29C 70/42* (2013.01); *B29C 70/54* (2013.01); *B32B 27/08* (2013.01); *B32B 27/281* (2013.01); *C23C 18/166* (2013.01); *C23C 18/1641* (2013.01); *C23C 18/1653* (2013.01); *C23C 18/1657* (2013.01); *C23C 18/22* (2013.01); *C23C 18/30* (2013.01); *C23C 18/32* (2013.01); *C23C 28/021* (2013.01); *C23C 28/023* (2013.01); *C25D 1/003* (2013.01); *C25D 1/02* (2013.01); *C25D 1/20* (2013.01); *C25D 3/02* (2013.01); *C25D 5/06* (2013.01); *C25D 5/54* (2013.01); *C25D 5/56* (2013.01); *C25D 7/00* (2013.01); *C25D 7/04* (2013.01); *C25D 9/02* (2013.01); *C25D 17/12* (2013.01); *G01B 7/16* (2013.01); *G01D 5/12* (2013.01); *G01N 3/08* (2013.01); *B29K 2079/08* (2013.01); *B29K 2105/0058* (2013.01); *B29K 2105/12* (2013.01); *B29K 2105/251* (2013.01); *B29K 2105/253* (2013.01); *B29K 2307/04* (2013.01); *B29K 2309/08* (2013.01); *B29L 2009/008* (2013.01); *B29L 2031/082* (2013.01); *B32B 2250/02* (2013.01); *B32B 2255/10* (2013.01); *B32B 2255/205* (2013.01); *B32B 2262/101* (2013.01); *B32B 2262/106* (2013.01); *B32B 2603/00* (2013.01); *B33Y 10/00* (2014.12); *B33Y 70/00* (2014.12); *B33Y 80/00* (2014.12); *G01N 2203/026* (2013.01); *G01N 2203/0268* (2013.01); *G01N 2203/0298* (2013.01)

(58) Field of Classification Search
USPC .............................. 205/117; 204/224 R, 225
See application file for complete search history.

(56) References Cited

U.S. PATENT DOCUMENTS

| | | | |
|---|---|---|---|
| 4,037,076 A * | 7/1977 | Blackaby | B23K 26/0823 219/121.61 |
| 4,998,448 A * | 3/1991 | Ellis, Jr. | F16F 15/32 156/330 |
| 5,132,191 A | 7/1992 | Zarnoch | |
| 5,180,639 A | 1/1993 | Zarnoch | |
| 5,225,059 A | 7/1993 | Penrose | |
| 5,277,785 A | 1/1994 | Van Anglen | |
| 5,411,795 A | 5/1995 | Silverman | |
| 6,159,589 A | 12/2000 | Isenberg et al. | |
| 6,322,730 B1 | 11/2001 | Wachtler | |
| 6,422,528 B1 | 7/2002 | Domeier et al. | |
| 6,511,463 B1 | 1/2003 | Wood et al. | |
| 6,655,208 B1 * | 12/2003 | McClanahan | F16C 3/02 73/460 |
| 7,320,832 B2 | 1/2008 | Palumbo et al. | |
| 7,354,354 B2 | 4/2008 | Palumbo et al. | |
| 7,387,578 B2 | 6/2008 | Palumbo et al. | |
| 7,553,553 B2 | 6/2009 | Palumbo et al. | |
| 7,565,418 B2 | 7/2009 | Ferrari et al. | |
| 7,591,745 B2 | 9/2009 | Palumbo et al. | |
| 7,771,289 B2 | 8/2010 | Palumbo et al. | |
| 7,803,072 B2 | 9/2010 | Palumbo et al. | |
| 7,824,774 B2 | 11/2010 | Palumbo et al. | |
| 7,827,252 B2 | 11/2010 | Hopmann et al. | |
| 7,910,224 B2 | 3/2011 | Palumbo et al. | |
| 7,925,729 B2 | 4/2011 | Bush et al. | |
| 8,025,979 B2 | 9/2011 | Palumbo et al. | |
| 8,129,034 B2 | 3/2012 | Palumbo et al. | |
| 8,463,890 B2 | 6/2013 | Bush et al. | |
| 8,484,332 B2 | 7/2013 | Bush et al. | |
| 8,671,184 B2 | 3/2014 | Bush et al. | |
| 2004/0180726 A1 * | 9/2004 | Freeman | F16C 3/02 464/180 |
| 2004/0197478 A1 | 10/2004 | Takagi | |
| 2006/0135281 A1 | 6/2006 | Palumbo et al. | |
| 2006/0135282 A1 | 6/2006 | Palumbo et al. | |
| 2006/0160636 A1 | 7/2006 | Palumbo et al. | |
| 2007/0111568 A1 | 5/2007 | Ferrari et al. | |
| 2007/0130286 A1 | 6/2007 | Hopmann et al. | |
| 2007/0209447 A1 | 9/2007 | Christ, Jr. et al. | |
| 2007/0279748 A1 | 12/2007 | Barth et al. | |
| 2007/0281176 A1 | 12/2007 | Palumbo et al. | |
| 2008/0090066 A1 | 4/2008 | Palumbo et al. | |
| 2008/0107805 A1 | 5/2008 | Palumbo et al. | |
| 2008/0119307 A1 | 5/2008 | Palumbo et al. | |
| 2008/0223172 A1 * | 9/2008 | Pullen | B23K 1/0008 74/572.4 |
| 2008/0254310 A1 | 10/2008 | Palumbo et al. | |
| 2009/0004465 A1 | 1/2009 | Kano et al. | |
| 2009/0019141 A1 | 1/2009 | Bush et al. | |
| 2009/0242410 A1 * | 10/2009 | Castro | C25D 3/12 205/118 |
| 2009/0298624 A1 | 12/2009 | Palumbo et al. | |
| 2010/0003538 A1 | 1/2010 | Nikolov et al. | |
| 2010/0028714 A1 | 2/2010 | Palumbo et al. | |
| 2010/0030495 A1 | 2/2010 | Jackson | |
| 2010/0047458 A1 | 2/2010 | Kohtoku et al. | |
| 2010/0143706 A1 | 6/2010 | Sun et al. | |
| 2010/0304171 A1 | 12/2010 | Tomantschger et al. | |
| 2011/0003171 A1 | 1/2011 | Palumbo et al. | |
| 2011/0014488 A1 | 1/2011 | Palumbo et al. | |
| 2011/0143159 A1 | 6/2011 | Palumbo et al. | |
| 2011/0167141 A1 | 7/2011 | Bush et al. | |
| 2011/0167145 A1 | 7/2011 | Bush et al. | |
| 2011/0167154 A1 | 7/2011 | Bush et al. | |
| 2012/0103111 A1 | 5/2012 | Baller et al. | |
| 2012/0121923 A1 | 5/2012 | Palumbo et al. | |
| 2012/0121927 A1 | 5/2012 | Nikolov et al. | |
| 2012/0134809 A1 | 5/2012 | Bagepalli et al. | |

(56) References Cited

U.S. PATENT DOCUMENTS

| | | | |
|---|---|---|---|
| 2012/0237789 A1 | 9/2012 | Wang et al. | |
| 2012/0244277 A1* | 9/2012 | Anders | B23K 9/046 427/123 |
| 2012/0247966 A1* | 10/2012 | Arndt | B82Y 30/00 205/109 |
| 2012/0287248 A1 | 11/2012 | Erdman, III et al. | |
| 2012/0301298 A1* | 11/2012 | Franks | F01D 5/027 416/144 |
| 2016/0145747 A1 | 5/2016 | Watson et al. | |
| 2016/0145755 A1 | 5/2016 | Cook | |
| 2016/0318062 A1* | 11/2016 | Zhai | B05D 1/12 |
| 2017/0292380 A1* | 10/2017 | Diwinsky | F01D 25/285 |

FOREIGN PATENT DOCUMENTS

| | | |
|---|---|---|
| JP | H11248407 | 9/1999 |
| JP | 2002054902 A | 2/2002 |
| JP | 2011017056 A | 1/2011 |
| WO | 0061831 A1 | 10/2000 |
| WO | 2004001102 A1 | 12/2003 |

OTHER PUBLICATIONS

International Search Report and Written Opinion for International application No. PCT/US2014/045947; International filing date: Jul. 9, 2014; dated Apr. 27, 2015; 11 pgs.

International Search Report for International application No. PCT/US2014/045902; International filing date: Jul. 9, 2014; dated Oct. 24, 2014; 4 pgs.

International Search Report for International application No. PCT/US2014/045912; International filing date: Jul. 9, 2014; dated Jun. 26, 2015; 3 pgs.

International Search Report for International application No. PCT/US2014/045930; International filing date: Jul. 9, 2014; dated Oct. 17, 2014; 2 pgs.

International Search Report for International application No. PCT/US2014/045937; International filing date: Jul. 9, 2014; dated Oct. 24, 2014; 4 pgs.

International Search Report for International application No. PCT/US2014/045962; International filing date: Jul. 9, 2014; dated Oct. 30, 2014; 2 pgs.

International Search Report for International application No. PCT/US2014/045972; International filing date: Jul. 9, 2014; dated Oct. 30, 2014; 2 pgs.

International Search Report for International application No. PCT/US2014/045945; International filing date: Jul. 9, 2014; dated Apr. 27, 2015; 3 pgs.

International Written Opinion for International application No. PCT/US2014/045912; International filing date: Jul. 9, 2014; dated Jun. 26, 2015; 8 pgs.

Schaedler, T.A. et al. Ultralight metallic microlattices, Science (Epub. Nov. 18, 2011), vol. 334, No. 6058, pp. 962-965.

Tierno, Pietro et al. Using electroless deposition for the preparation of micron sized polymer/metal core/shell particles and hollow metal spheres, J. Phys. Chem. B 2006 (Epub. Feb. 16, 2006), vol. 110, No. 7, pp. 3043-3050.

\* cited by examiner

IN-SITU BALANCING OF PLATED POLYMERS

CROSS-REFERENCE TO RELATED APPLICATIONS

This application claims priority under 35 U.S.C. § 119(e) to U.S. Provisional Patent Application Ser. No. 61/844,030 filed on Jul. 9, 2013.

FIELD OF THE DISCLOSURE

This disclosure relates to methods for the in-situ balancing of plated polymers. More specifically, this disclosure relates the balancing a rotatable component in place by rotating the component and brush plating or brush electroplating a metal layer onto the component until the component until it is balanced. Additionally, this disclosure relates the in-situ balancing of rotatable components by attaching a balancing weight to component, rotating the component, and then brush plating or brush electroplating the component and balancing weight until the component is balanced.

BACKGROUND

Metallic parts tend to be heavy due to the high densities of most metals. Typically, there are areas of a metallic part that are lightly loaded or not loaded (little or no stress) as well as highly loaded (or stressed) areas. An ideal metallic part would contain a sufficient amount of metal in high-stress areas to transmit the necessary loads and perform the function of the part. Such an ideal part would also contain less or no metal in areas with little or no stress, thereby reducing the weight of the metallic part to an idealized minimum. In some cases, removing metal from a metallic part can lead to weight savings. However, removing metal from a metallic part by conventional means, such as machining, laser drilling, etc., can be both difficult and costly. Further, removing material from a metallic part can lead to reduced material properties of the part, which may be unacceptable for its intended application. Therefore, there is a need for improved and/or lower-cost methods of producing metal parts that are lightweight but strong enough in high-stress areas to perform the function(s) of the part.

There is an ongoing effort to replace metal components in a gas turbine engine with lighter components made from alternative materials, even if the components experience significant loads or are subjected to environmental concerns (e.g., high or low temperatures, erosion, foreign-object damage) during use. For example, in the aerospace industry, manufacturers of gas turbine engines are considering the use of alternative materials for fan blades, compressor blades, and possibly turbine blades. Suitable non-metal alternative materials include, but are not limited to, reinforced polymers, polymer matrix composites, ceramics, and ceramic matrix composites.

Blow molding processes begin with melting the molding material and forming it into a parison or preform. The parison is a tube-like piece of plastic with a hole in one end through which compressed air can pass through. The parison is clamped into a mold and air is pumped into the parison. The air pressure pushes the molding material outwards to match the interior surface of the mold. Once the molding material has cooled and hardened, the mold opens and the part is ejected. In contrast, injection molding includes injecting molding material for the part into a heated barrel, mixing and forcing the molding material into a mold cavity where the molding material cools and hardens to the configuration of the cavity. Compression molding is a method of molding in which the preheated molding material is placed in an open-mold cavity. The mold is closed and pressure is applied to force the material into contact with all mold areas while heat and pressure are maintained until the molding material has cured.

For many molding processes, hard tooling is used to form the mold or die. While hard tooling can provide high dimensional repeatability, hard tooling is very heavy and cumbersome and can present a safety hazard when moved or handled. Further, fabricating hard tooling is time consuming and costly. As a result, hard tooling is normally too expensive and time consuming for short production runs and/or for the fabrication of test parts. Thus, the ability to quickly fabricate tooling to support short production runs and/or test runs of composite materials is desired.

Blow molding and injection molding cannot be used if the plastic to be molded is in the form of a composite with a plurality of layers or plies, i.e., a composite layup structure. Composites are materials made from two or more constituent materials with different physical or chemical properties that, when combined, produce a material with characteristics different from the individual components. The individual components remain separate and distinct within the finished structure. Typically, composite layup structures can be molded or shaped using compression molding, resin transfer molding (RTM), or vacuum assisted resin transfer molding (VARTM), all of which utilize hard tooling that typically include details machined into one or more blocks of metal that form the mold.

Composites can also include reinforcing fibers or matrices. The fibers or matrices may be formed from ceramics, metals, polymers, concrete, and various other inorganic and organic materials. Organic matrix composites (OMCs) may include polyimides and/or bismaleimides (BMIs) because they can be used at higher temperatures than other commonly used organic reinforcing materials, such as epoxies. Such high-temperature OMCs may be processed by autoclave molding, compression molding, or resin-transfer molding. These processes all require lengthy cure and post-cure cycles as well as hard tooling that is difficult and costly to make. Thus, improved methods for molding OMCs are also desired.

Electrolytic and electroless plating are inexpensive methods of forming a metallic layer on a surface of a molded plastic article. To ensure adhesion of the plated layer to the molded plastic article, the surface of the plastic article may need to be prepared by etching, abrading, or ionic activation. The most common types of metals used for plating molded plastic include copper, silver, and nickel, although other metals may be used.

Electrolytic plating is the deposition of a metal on a conductive material using an electric current. A molded plastic article must first be made conductive to be electrolytically plated. This can be done through a multi-step process that typically involves the application of a catalyst, electroless plating of Ni, and electrolytic plating of Cu. The article to be electrolytically plated is then immersed in a solution of metal salts connected to a cathodic current source, and an anodic conductor is immersed in the bath to complete the electrical circuit. Electric current flows from the cathode to the anode, and the electron flow reduces the dissolved metal ions to pure metal on the cathodic surface. Soluble anodes are made from the metal that is being plated and dissolve during the electroplating process, thereby replenishing the bath.

A closely related process is brush electroplating, in which localized areas or entire items are plated using a brush saturated with plating solution. The brush may be a stainless steel body wrapped with a cloth material that both holds the plating solution and prevents direct contact with the item being plated. The brush may be connected to the positive side of a low-voltage direct-current power source, and the item to be plated connected to the negative side. The operator dips the brush in plating solution then applies it to the item to be plated, moving the brush continually to get an even distribution of the plating material. Brush electroplating has several advantages over tank plating, including portability, ability to plate items that for some reason cannot be tank plated (e.g., plating portions of very large decorative support columns in a building restoration), low or no masking requirements, and comparatively low plating solution volume requirements. Disadvantages compared to tank plating can include greater operator involvement (tank plating can frequently be done with minimal attention), and inability to achieve a plate as thick as can be achieved using tank plating.

Measuring strain on rotating components has historically been problematic and involves sending data out to stationary data acquisition systems via split-ring electrical coupling or radio frequency (RF) transmission devices. Strain gages, the associated wiring, and/or the mass and volume of a radio transmitter can interfere with the operation of a component, especially if balancing is critical, if the space envelope surrounding the component is tight, or if airflow over a surface of the component is involved. Measuring strain on rotating components is important to accurately assess component failure, whether it is made from a traditional alloy or from an aforementioned alternative material.

Plated polymeric mechanical test specimens are needed to accurately characterize the stress and strain imposed on a plated polymeric structure. Test specimens that are completely encapsulated in metal plating are not preferred because such an encapsulated specimen does not simulate a semi-infinite medium, which best approximates plated polymer walls in actual parts. It is more helpful to cut test specimens out of larger plated panels to provide exposed edges (a sandwich structure) approximating a semi-infinite medium. Preliminary testing of plated polymers demonstrates that tensile testing of thick-plated polymers cannot be reliably accomplished by gripping standard test specimen geometries, such as the test specimens specified by ASTM D638. Gripping a standard, plated test specimen results in either (1) too much slippage to accurately or reliably calculate ultimate load, displacement, and strain values, or (2) the test specimen being crushed in the grip region, resulting in stress concentrations, significant strain outside of the gage area, and premature failure.

Therefore, there is a need for improved methods and apparatuses for measuring strain imposed on parts, including rotating components, that may be made from alternative materials such as polymers, reinforced polymers, polymer matrix composites, ceramics, and ceramic matrix composites.

SUMMARY OF THE DISCLOSURE

In one aspect of the present disclosure, a method for balancing a rotatable component is disclosed. The method may comprise, rotating the component and plating the component to deposit a metal layer onto the component until the component is balanced.

In a refinement, the plating may be selected from the group consisting of brush plating and brush electroplating.

In another refinement, the brush plating may comprise a brush saturated with plating solution.

In another refinement, the brush may be selected from the group consisting of stainless steel or graphite.

In another refinement, the brush may be further wrapped with a cloth material that holds the plating solution and prevents direct contact with the part being plated.

In another refinement, the brush electroplating may comprise a brush saturated with plating solution.

In another refinement, the brush may be selected from the group consisting of stainless steel or graphite.

In another refinement, brush may be further wrapped with a cloth material that holds the plating solution and prevents direct contact with the part being plated.

In accordance with another aspect of the present disclosure, a method for balancing a rotatable component is disclosed. The method may comprise attaching a balancing weight to the rotatable component, rotating the component, and plating the component and the balancing weight to deposit a metal layer onto the balancing weight and the component until the component is balanced.

In a refinement, the plating may be selected from the group consisting of brush plating and brush electroplating.

In another refinement, the brush plating may comprise a brush saturated with plating solution.

In another refinement, the brush may be selected from the group consisting of stainless steel or graphite.

In another refinement, the brush may be further wrapped with a cloth material that holds the plating solution and prevents direct contact with the part being plated.

In another refinement, the brush electroplating may comprise a brush saturated with plating solution.

In another refinement, the brush may be selected from the group consisting of stainless steel or graphite.

In another refinement, the brush may be further wrapped with a cloth material that holds the plating solution and prevents direct contact with the part being plated.

In another refinement, the balancing weight may be selected from the group consisting of metals, metal powder filled resins and polymers.

In accordance with another aspect of the present disclosure, a method for balancing a rotatable fan assembly is disclosed. The method may comprise attaching a balancing weight to a fan assembly, rotating the fan assembly, followed by plating the fan assembly and the balancing weight to deposit a metal layer onto the balancing weight and fan assembly until the fan assembly is balanced.

In a refinement, the balancing weight may be selected from the group consisting of metals, metal powder filled resins and polymers.

In another refinement, the plating may be selected from the group consisting of brush plating and brush electroplating.

Figure 1A:
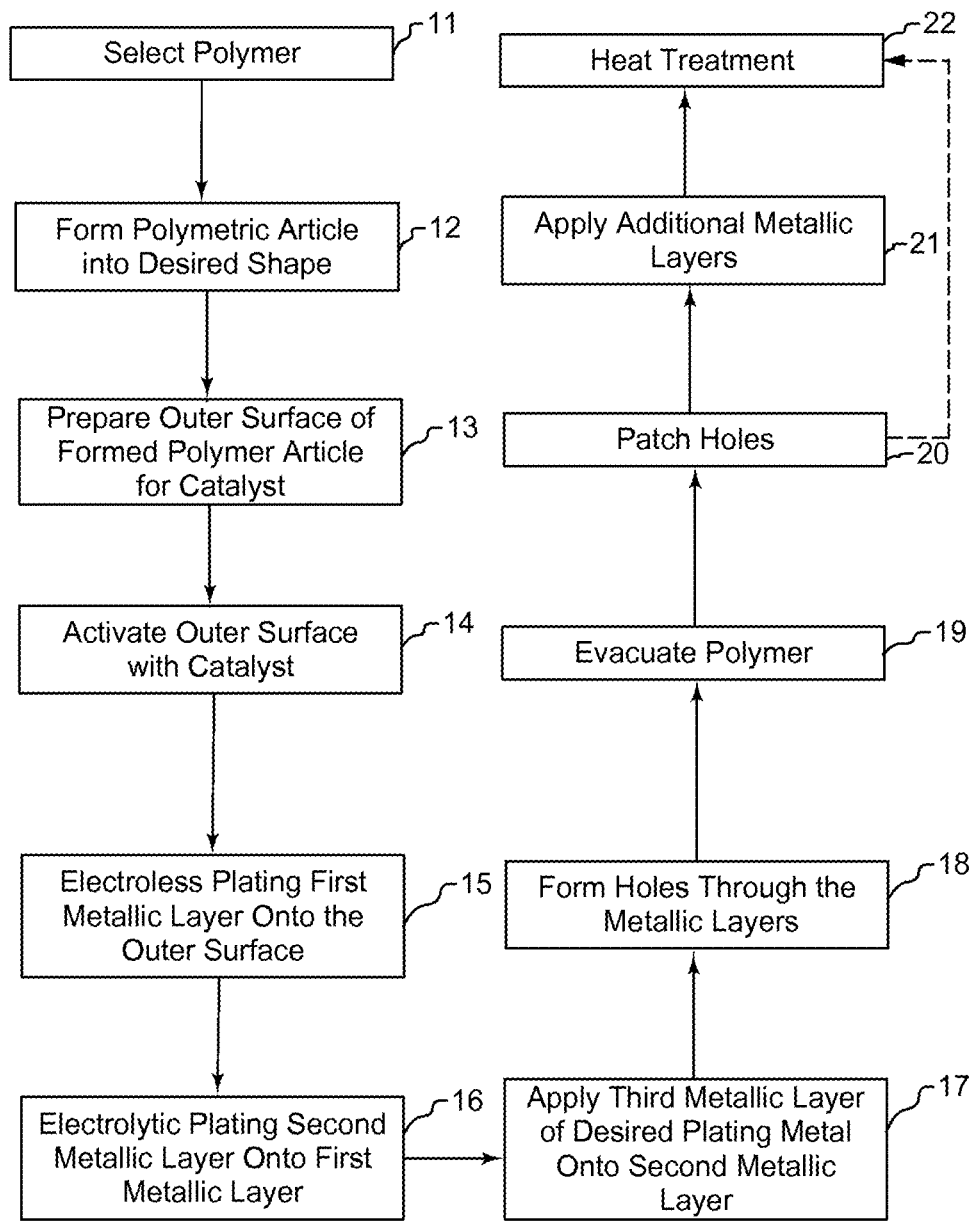
FIG. 1A is a flow diagram illustrating the disclosed methods of forming lightweight metal parts.

While the exemplary rotating component shown in the drawings is a fan blade assembly, it will be apparent to those skilled in the art that the disclosed strain measurement system and methods of measuring strain imparted to a rotating component may be utilized in connection with compressor blades, turbine blades, propeller blades, wheels, or other components that may be fabricated from non-traditional, non-metal, or alternative materials that are subject to strain when the component is rotated.

DETAILED DESCRIPTION

Lightweight Parts and Components Produced from Plating Molded Polymeric Substrates FIG. 1A illustrates various disclosed methods for forming lightweight parts and components in accordance with this disclosure. In part 11, a polymer is selected for forming a desired shape or geometry from which the part will be created. Typically, the polymer will be acrylonitrile butadiene styrene (ABS), polytetrafluoroethylene (PTFE), or an ABS/polycarbonate blend. These polymers are mentioned here because they are compatible with most etching solutions. However, other polymers that are compatible with the selected etching solution or other evacuation method may be utilized, as will be apparent to those skilled in the art. In part 12, the polymer is formed or molded into the desired shape or geometry for the metal structure.

The forming of the polymer may be carried out in any of a variety of ways, such as additive manufacturing, injection molding, compression molding, blow molding, extrusion molding, thermal forming, transfer molding, reaction injection molding, and, if applicable, combinations thereof, or other suitable forming process as will be apparent to those skilled in the art. In part 13, if necessary, the outer surface of the formed polymer may be prepared for receiving a catalyst for the subsequent plating process(es). The outer surface may be prepared in a variety of ways, such as etching, abrading, reactive ion etching, ionic activation, deposition of a conductive material such as graphite, silver paint, gold sputter, etc. and, to the extent applicable, combinations thereof.

The metals used for plating may include nickel, cobalt, iron, copper, gold, silver, palladium, rhodium, chromium, zinc, tin, cadmium, and alloys of the foregoing elements comprising at least 50 wt. % of the alloy, although other metals can be used. The plating process can be extended to a range of non-metal substrates, including, but not limited to, polymer, reinforced polymer, polymer matrix composite, ceramic, ceramic matrix composite, etc.

In part 14, the outer surface of the formed polymer may be activated by applying a catalyst. Typically, the catalyst is palladium although platinum and gold are other possibilities. The catalyst may be applied to a thickness on the atomic scale. Prior to the application or activation with the catalyst, the formed polymer may be rinsed or neutralized, especially if an etching process is carried out. Subsequent to the activation with a catalyst, an accelerator may be optionally applied. In part 15, a first layer of metal is deposited onto the outer surface of the formed polymer using an electroless plating method. Typically, the metal used to form the first layer via electroless plating is nickel, although copper, gold, and silver are other possibilities. After the first layer is formed on the outer surface of the formed polymer to form a metal structure, if the desired thickness for the metal structure has not been reached or additional material properties are desired, a second layer of metal may optionally be deposited on the first layer by electrolytic plating in part 16. If the second layer is not to be succeeded by a third layer, the second layer may be formed from a metal that is the desired material for the finished part.

Electrolytic plating is the deposition of a metal on a conductive material using an electric current. A component made from a non-metal material must first be made conductive to be electrolytically plated. This can be done through electroless plating or by the use of conductive additives such as carbon. The article to be electrolytically plated is immersed in a solution of metal salts connected to a cathodic current source, and an anodic conductor is immersed in the bath to complete the electrical circuit. Electric current flows from the cathode to the anode, and the electron flow reduces the dissolved metal ions to pure metal on the cathodic surface. Soluble anodes are made from the metal that is being plated, thereby replenishing the bath.

The polymer may be evacuated after the first or second layers are deposited, but it may be preferable to apply successive layer(s) of metal to the structure wherein the successive layer(s) may be formed from a metal that is the desired material for the finished part. The application of the optional successive layer(s) of desired material may be carried out in a variety of ways including, but not limited to electroplating, electroless plating, electroforming, thermal spray coating, plasma vapor deposition, chemical vapor deposition, cold spraying, and other techniques that will be apparent to those skilled in the art. The successive layer(s) of desired metal may be applied in part 17 as shown in FIG. 1A. In part 18, at least one hole may be formed through the structure for purposes of evacuating the polymer in part 19, unless such a hole is an integral feature of the structure. The hole may be formed after formation of the first layer, optional second layer, optional successive layer, or at any time after the structure is sufficiently strong. The hole may be patched at part 20 prior to a final heat treatment or prior to the application of additional metallic layers in part 21. A final heat treatment can be carried out at part 22 or the layer(s) may be alloyed via a bonding treatment, such as transient liquid phase (TLP) bonding, brazing, diffusion bonding, or other alloying means known to those skilled in the art.

The final metallic part may be hollow or may be filled with a reinforcing filler material or the polymeric article may be of a structure that has material properties to render it suitable for remaining within the final metallic part in a partially etched or removed state. Suitable materials for such reinforcing filler material are a metallic or polymeric foam, although other suitable filler materials will be apparent to those skilled in the art.

Anti-Counterfeiting Tags

Counterfeiting has a long and ignoble history, ranging from art and literature to manufactured goods, particularly replacement parts. Further, counterfeiting in the aerospace, automotive, or other transportation industries, for example, may have serious consequences as the use of an inferior counterfeit replacement part may create a safety hazard. Thus, there is a need to effectively reduce the introduction of counterfeit parts into supply chains in general and a more urgent need to reduce the presence of counterfeit parts in supply chains of industries where the use of counterfeit parts creates safety concerns.

An anti-counterfeiting tag may be added to a plated polymeric article and therefore the final part. In such an embodiment, the anti-counterfeiting tag should be detectable through the plated structure by an appropriate sensor. Such anti-counterfeiting tags may include a material of a different density than the polymer(s) used to fabricate the article, a low-level radioisotope, an RFID tag that is detectable through the plated metal structure, a particular chemical that can be sensed in the molded plastic article and through the plated metal structure, or another identifier useful for anti-counterfeiting purposes as will be apparent to those skilled in the art.

If the article is molded, the anti-counterfeiting tag may be co-molded with the article or a protrusion can be included in the mold tool to provide a recess for housing the anti-counterfeiting tag. Alternatively, a slot can be machined in the polymeric article using any manufacturing process to allow for the anti-counterfeiting tag. A polymeric plug may be bonded over the exposed surfaces of the anti-counterfeiting tag to provide a completely polymeric surface for post plating. In another embodiment, the article may be a polymeric composite layup structure with a plurality of plies or layers and the anti-counterfeiting tag may be disposed between adjacent plies or layers of the layup structure.

Composite Molded Polymeric Articles

As noted above, the shaped polymeric article may be for use as a mold and can be formed using one of the molding processes described above and which can be plated with at least one metallic layer to form an inexpensive metal tooling that can be economically used to support short production runs and/or the fabrication of test parts or components. The shaped polymeric article may also be base for a gauge, other instrument or prototype hardware that can be fabricated by coating the shaped polymeric article with one or more metallic layers.

When the plated polymer component is used for tooling, it may be advantageous to form the article with a composite layup structure formed from one or more of the following: polyetherimide (PEI); polyimide; polyether ether ketone (PEEK); polyether ketone ketone (PEKK); polysulfone; nylon; polyphenylsulfide; polyester; and any of the foregoing with fiber reinforcement e.g., carbon fiber, glass-fiber, etc. The composite layup structure may be compression molded into a desired shape to from a composite article. One or more metallic layers may be deposited onto the composite article to form a structure. If the structure is to be used as tooling for a short term production or for the production of test parts, the metallic layer(s) may applied by electroless plating, electroplating, or electroforming with a thickness ranging from about 2.54 to about 1270 microns (about 100 to about 5e+004 microinches), more typically from about 101.6 to about 1016 microns (about 4000 to about 4e+004 microinches). This thickness range may provide sufficient resistance to wear and impact, and/or provide the ability to meet tight tolerance requirements and/or provide a surface finish that will be transferred to the molded part.

The plated metallic layer(s) that forms the tooling structure may include one or more layers. Plating may be performed in multiple steps by masking certain areas of the molded article to yield different thicknesses or no plating in certain areas. A customized plating thickness profile can also be achieved by tailored racking (including shields, thieves, conformal anodes, etc.). Tailored racking allows for an optimization of properties for the mold tooling with respect to heat resistance, structural support, surface characteristics, etc. without adding undue weight to the tooling to completely accommodate each of these properties individually. Plating thicknesses may be tailored to the structural requirements of the mold tooling.

Some mounting features (e.g., flanges or bosses) may be bonded to the molded article using a suitable adhesive after molding but before plating to simplify the mold tooling. Further, the polymer or composite article can be fabricated in multiple segments that are joined by any conventional process (e.g., by welding, adhesive, mitered joint with or without adhesive, etc.) before plating. Furthermore, molded composite articles may be produced and plated separately and subsequently bonded by transient liquid phase (TLP) bonding. In addition, features such as bosses or inserts may be added (using an adhesive, riveting, etc.) to the plated structure or tooling after the plating has been carried out. When the molded article is to be used as a substrate formed by injection molding and to be plated for use in a tooling, the article may have a thickness ranging from about 1.27 to about 6.35 mm (about 0.05 to about 0.25 inch), with localized areas ranging up to 12.7 mm (0.5 inch). In contrast, compression molding can be used to form a molded article with a wall thicknesses ranging from about 1.27 to about 51 mm (about 0.05 to about 2.008 inch).

For some parts with complex geometries and/or that are large, multiple-piece mold toolings are required because the molded part cannot be reliably released from a single mold. Thus, to fabricate tooling for such a part with complex geometry and/or that is large, the part may be divided into a plurality of segments, which may be coupled. Possible weak points caused by the joining of two segments together may be overcome by joining the two segments using one or more joints in combination an adhesive that remains within the joint so that the adhesive is not exposed to or "visible" to a subsequent plating process. The types of joints that may be suitable for coupling two such polymer segments together include mitered joints, angled joints, angled-mitered joints, welded joints with covers, mitered joints with low angle boundaries, mitered joints with accommodation channels for accommodating extra adhesive, welded joints with a cover, slot-type attachments with our without an additional fastener, and others as will be apparent to those skilled in the art. Then, the two segments are plated together using one of the plating methods described above. By plating one or more layers over the joint and over the outer surfaces of two segments, possible structural weak points created by the coupling of the two segments are avoided. Suitable adhesives include epoxy-based adhesives in liquid, paste, or film form, with long-term service temperatures of up to 121° C. (249.8 degree Fahrenheit), and bismaleimide-based adhesives with service temperatures of up to 177° C. (350.6 degree Fahrenheit) (in paste or film form). In addition, cyanoacrylates and polyurethanes could be used in certain situations, depending upon the strength and rigidity requirements.

The plating material and thickness may be selected such that a structural analysis would indicate that the plating layer will take the majority of the loads that the part experiences. Furthermore, geometric features are optionally added into the design to mitigate any weakness caused by the joining to two segments together prior to the plating.

Temporary or short-run tooling may be made using the disclosed methods, particularly if the molded article is fabricated from a composite layup structure that is sufficiently stiff, but which can be compression molded. The compression molded composite article serves as a substrate that may be plated to form a tooling.

Plating of Joined Polymeric Articles

Conventional processes for fabricating polymeric parts (e.g., injection or compression molding) have limitations with respect to geometric complexity and part size. In particular, large parts (by volume or weight) may exceed the capabilities of available injection molding machines or compression presses. Complex geometry or features within a part may also make it difficult to form and successfully release the part from the mold tooling. Complex geometries or features may also require very intricate multi-piece mold designs.

Therefore, an ability to fabricate separate part details and join them into an assembly may offer cost benefits in these situations. By plating a polymeric part with a suitable plating material to a suitable thickness, the structural weak points that are caused by bonding may be overcome.

An exemplary substrate may be a molded structure formed of at least one material selected from the group consisting of: polyetherimide (PEI); polyimide; polyether ether ketone (PEEK); polysulfone; Nylon; polyphenylsulfide; polyester; and any of the foregoing with fiber reinforcements e.g., carbon fibers or glass-fibers. Suitable adhesives for joining the molded substrates include epoxy-based adhesives in liquid, paste or film form, with long-term service temperatures for aerospace applications of up to 250° F. (121° C.), and bismaleimide (BMI) based adhesives in paste or film forms with service temperatures of up to 350° F. (177° C.). Also, cyanoacrylates and polyurethanes could be used in selected cases depending on strength and rigidity requirements.

Figure 1B:
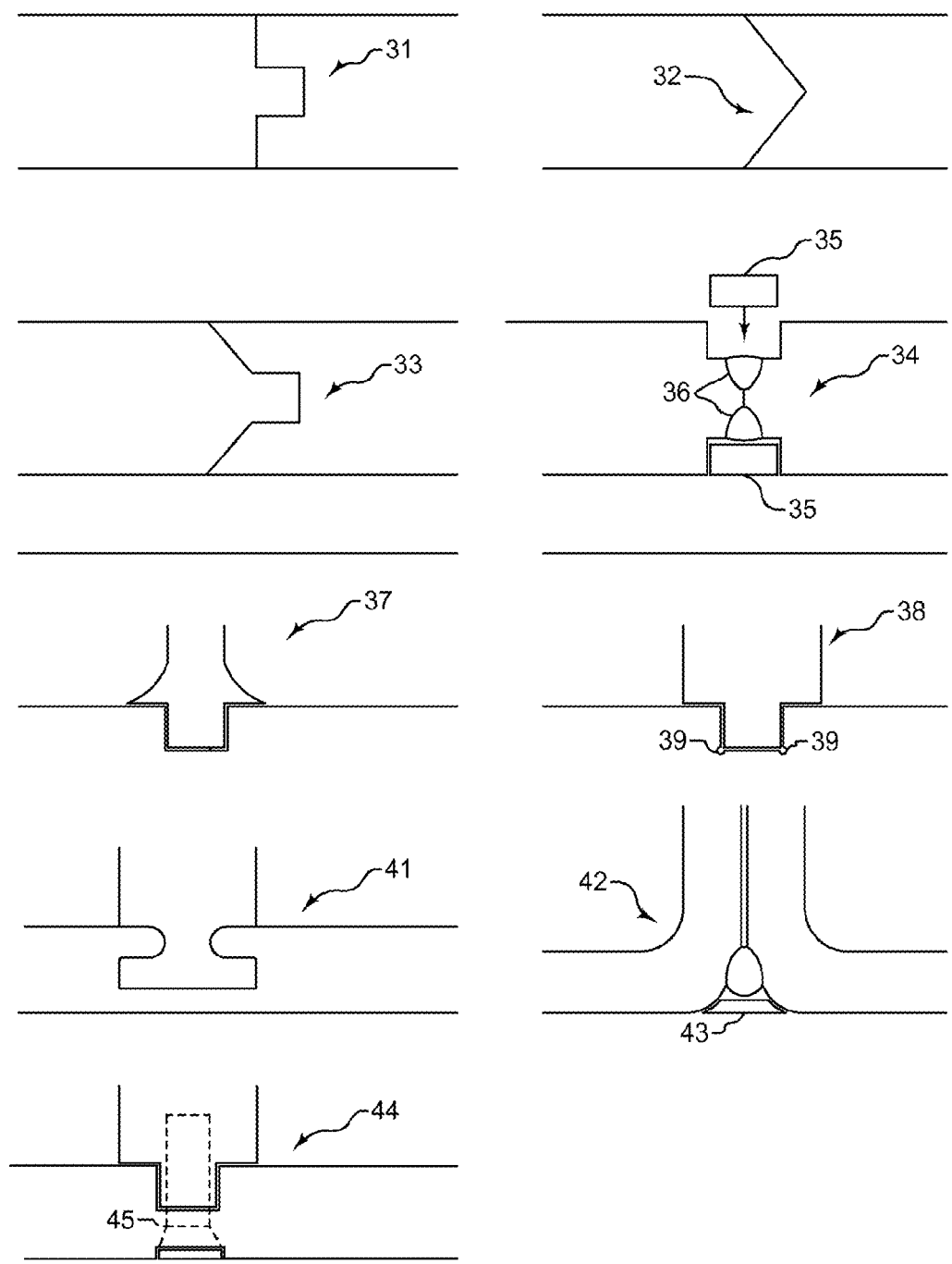
FIG. 1B illustrates, schematically, various means for joining two molded polymeric components together prior to plating.

Plating on adhesives can be difficult and causes deviations in plating properties. FIG. 1B schematically illustrates a variety of methods or joints that can be used to join polymeric substrate segments together so that bond line effects are minimized and only the polymeric material is visible to the plating process. The methods or joints include, but are not limited to a mitered joint 31, an angled joint 32, an angled mitered joint 33, a welded joint 34 with covers 35 that may be press-fit into place or secured with adhesive or weld beads 36, a mitered joint 37 with low angle boundaries, a mitered joint 38 with accommodation channels 39 for extra adhesive, a slot attachment-type joint 41, a welded T-joint 42 with a cover 43, a mitered joint 44 attached with a fastener 45, and others as will be apparent to those skilled in the art. Further, two component halves may be joined to create one or more tortuous passages. Also, components with ducts of different cross sections may be economically molded and joined together. Any combination of these and similar methods can be used to create plated polymeric parts with geometries and/or sizes that are outside the limits or economic feasibility of conventional molding processes.

The plating material and thickness may be selected such that a structural analysis indicates that the plating layer will take the majority of the loads that the part experiences. Furthermore, geometric features are optionally added into the design to mitigate the bond line property knockdowns.

Thus, plated polymeric parts can be produced on a larger scale than the capacity limits of injection or compression-molding processes currently allow. Part geometries for plated polymeric parts can be more complicated than the injection or compression-molding processes can allow. Part cost can be reduced when complex parts that are difficult to mold are molded in multiple, simpler segments. The plating material and thickness are selected to accommodate weaknesses induced by bond lines and bonding methods.

Polyimide and Bismaleimide Resins

High temperature organic matrix composites (OMCs) such as polyimides and bismaleimides (BMIs) are typically formed into a desired shape by autoclave molding, compression molding or resin-transfer molding. These molding processes all require lengthy cure and post-cure cycles as well as costly mold toolings, which have long lead times. These molding methods are also limited in terms of the geometrical complexity of the desired shape of the molded article.

Additive manufacturing (AM) or three-dimensional (3D) printing is a process of making a three-dimensional solid object of virtually any shape from a digital model. AM is achieved using an additive process, wherein successive layers of material are laid down in different shapes. AM is considered distinct from traditional machining techniques, which mostly rely on the removal of material by methods such as cutting or drilling, i.e., subtractive processes. A materials printer usually performs AM processes using digital technology. Since the start of the twenty-first century there has been a large growth in the sales of these machines, and while the price has dropped substantially, AM remains very costly. Despite its high cost, AM is used in many fields, including aerospace.

In the disclosed methods, imidized polyimide resin and/or bismaleimide resin (BMI) may be used to form desired shapes by additive manufacturing (AM). The resins may be solids at room temperature and may be ground and sieved to the appropriate size for powder bed processing (SLS) or the solid resin can be melted for liquid bed processing (SLA). The resulting AM article can then be plated to provide additional strength, thermal capability, erosion resistance, etc., and combinations thereof. The plating layer may include one or more layers. The metallic layer may be applied by electroless plating, electroplating, or electroforming. One especially useful application is for wear parts such as bushings, liners, and washers, which have extensive applications in gas turbine engines and in other manufacturing industries.

Strain Measurement on Non-Metal Components with Plated Targets

Figure 2:
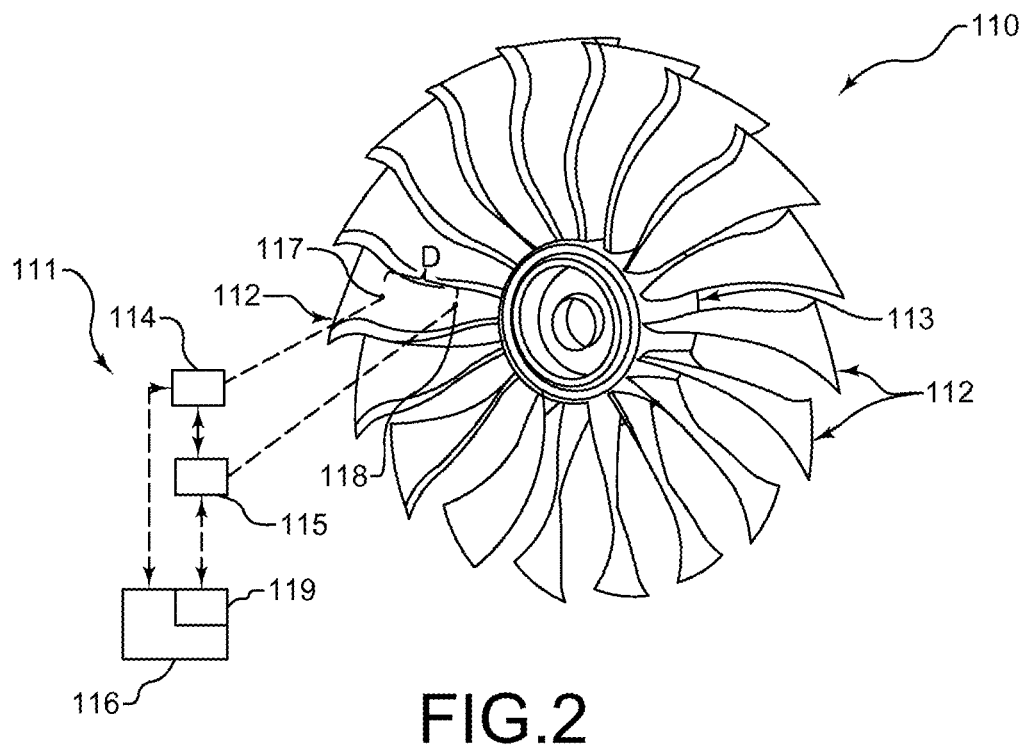
FIG. 2 is a perspective view of a rotating fan assembly that is coupled to a strain measurement system in accordance with this disclosure, wherein the strain measurement system is shown schematically.

FIG. 2 illustrates a fan blade assembly 110 that is coupled to a strain measurement system 111. The fan blade assembly 10 includes a plurality of fan blades 112 that are coupled to a rotor or disk 113. To save weight, the fan blades 112 may be fabricated from non-metallic materials, such as polymers, reinforced polymers, polymer matrix composites, ceramics, ceramic matrix composites, etc.

However, because failure of a fan blade 112 of a fan blade assembly 110 of a gas turbine engine presents a safety hazard, measuring the strain imposed on the fan blades 112 during rotation of the fan blade assembly 110 may be desirable. FIG. 2 therefore illustrates schematically a strain measurement system 111 that includes a first encoder 114 (or other suitable type of sensor), a second encoder 115 (or other suitable type of sensor), a controller 116, which may be integrated with the first and second encoders 114 and 115, respectively, a first electromagnetic target 117 disposed on the fan blade 112 and a second electromagnetic target 118, also disposed on the fan blade 112 and spaced apart from the first electromagnetic target 117 by a distance shown as D. The first and second electromagnetic targets may be plated onto the fan blade 112.

When the fan blade 112 is stationary, or is otherwise not under significant strain or stress, the first and second electromagnetic targets 117, 118 are spaced apart by an initial distance $D_1$. As the fan blade assembly 110 is rotated, the centrifugal forces experienced by the fan blade 112 may impart strain to the fan blade 112 thereby changing the distance between the first and second electromagnetic targets 117 and 118, respectively from the initial distance $D_1$ to an actual distance $D_2$. The first and second encoders 114 and 115, respectively, are designed to monitor the actual positions of the first and second electromagnetic targets 117 and 118, respectively. Those actual positions may be transmitted to the controller 116, which may be a separate component or which may be integral with the first and second encoders 114 and 115, respectively. The controller 116 may have a memory 119 that may be programmed with at least one program for determining the actual distance $D_2$ based upon the signals received from the first and second encoders 114 and 115, respectively. The memory 119 of the controller 116 may also be programmed with an algorithm for calculating strain imparted to the fan blade 112 during rotating thereof based on the differences between the actual distance $D_2$ and the initial distance $D_1$. Information relating to the strain imparted to the fan blade 112 may then be transmitted to the operator or pilot of the aircraft or the main control module of the aircraft.

Figure 3:
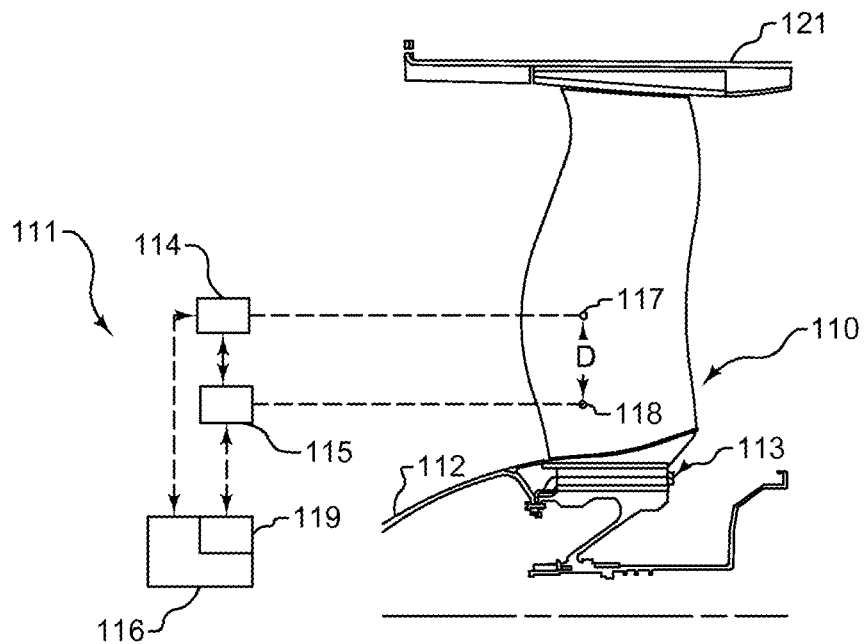
FIG. 3 is a side sectional view of a fan assembly coupled to a disclosed strain measurement system, which is shown schematically.

FIG. 3 illustrates the fan blade assembly 110 as disposed within a nacelle 121. FIG. 2 also partially illustrates the rotor 113 coupled to a nose cone 122. It will be noted that the encoders 114 and 115 may be different types of sensors and/or may incorporate Hall-effect sensors as well. If the encoders/sensors 114 and 115 incorporate Hall-effect sensors, the encoders/sensors 114 and 115 may also measure the rotational velocity of the fan blade 112.

Strain Measurement on Thick, Plated Polymer and/or Composite Components

Preliminary testing of plated polymers has demonstrated that tensile testing of thick-plated polymers cannot be reliably accomplished by using conventional gripping techniques on grip portions of standard test specimen geometries. This conventional method produces either (1) far too much slippage to accurately or reliably calculate ultimate load, displacement, and strain values, or (2) crushes the test specimen in the grip area, resulting in stress concentrations, significant strain outside of the gage area, and premature failure.

Using a 30% carbon-fiber-reinforced amorphous thermoplastic (polyetherimide, commonly known as ULTEM®) with 0.008 in (0.2 mm (0.007874 inch)) nominal Ni plating, the amount of slippage could be neglected for a Type IV specimen tested in accordance with the ASTM D638 protocol. In contrast, using a Type IV specimen and testing under ASTM D638 and with a 0.015 in (0.38 mm (0.01496 inch)) nominal Ni plating, the amount of slippage was severe enough that absolute displacement (and therefore strain) values could not be accurately obtained. As a solution to this problem, a pin-loaded tensile specimen in accordance with ASTM D638, Type IV may be used, preferably with two spaced-apart holes drilled therein to allow for pin loading of the specimen. For example, referring to FIG. 4, the overall length of the specimen 200 may be about 12.7 cm (5 inches) and the centers of the holes 201 may be spaced apart by about 9.616 cm (3.786 inches). The holes may have about a 0.653 cm (0.2571 inch) diameter and may be centered longitudinally in the wider end portions or the grip regions 202 of the Type IV specimen 200. The grip regions 202 may have a width of about 1.91 cm (0.752 inch). The arcs 203 connecting the grip regions 202 to the narrow middle gauge region 204 may have a radius of about 2.54 cm (1 inch). The length of the middle gauge region 204 may be about 3.175 cm (1.25 inches).

The hole 201 sizes may be optimized using certain parameters. For example, plating thickness, width of the gage region, hole diameter, and width between the hole edge and the specimen side edges, and end edge may be used to define a working space for test geometry.

Bushings 205 may be inserted in the holes 201 to carry the load more evenly. Alternatively, the holes 201 can be machined in the polymer before plating to provide plating in the loading holes 201. These holes 201 can incorporate fillets to prevent a buildup of plating (nodulation), or the buildup of plating that would otherwise occur should be machined off to prevent stress concentrations. Alternative hole shapes such as square, slot, and diamond can also be incorporated in flat specimen geometries. An alternative method is to machine the test specimen 200 before plating and mask the edges of the gage region 204 before plating, thereby providing for the exposed edges along the gage region 204 and completely encapsulating the grip regions 202. This method accommodates testing the specimen 200 for some thicker platings by gripping as the encapsulated grip regions 202, which provide increased resistance to crushing.

Figure 4:
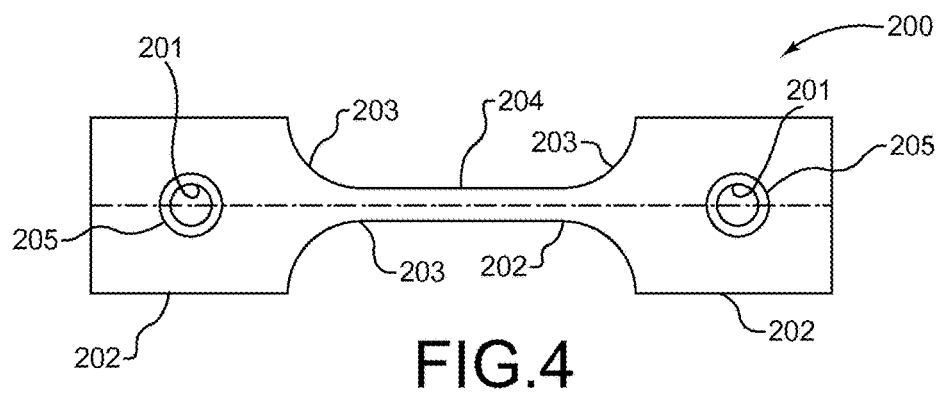
FIG. 4 is a plan view of a test specimen made in accordance with ASTM D638, Type IV, but with holes extending through both grip portions.

A range of alternate (non-flat) geometries can be used for the grip regions 202 to obtain accurate load-displacement data for plated polymeric structures using a flat gage region 204 with exposed edges (two-dimensional stress state). One such geometry for the grip regions 202 is conical, wherein the flat grip regions 202 of the test specimen 200 may be reconfigured into conically-shaped grip regions (not shown) on each end of the narrow middle gauge region of the test specimen 200, thereby accommodating loading by conical grips. In an I-beam configuration, a flat tensile specimen like that shown at 200 in FIG. 4 is provided, but with transverse members at or near the end of specimen instead of the conventional grip portions 202 shown in FIG. 4. The transverse members may be used to load the specimen using a clevis, hooks, loops, ledges, etc. This method can also accommodate flat sections or rods as the protruding components of the I-beam. In a flared configuration, a flat tensile specimen with flared edges at the ends thereof may provide for gripping using platens set at angles, thereby providing a hybrid between standard tensile grips and conical grips. If any sections of the test specimen geometries are prone to develop porosity during a molding process (e.g., injection molding), they can be hollowed out before forming. Further, reinforcing ribs can be added to hollow sections, as necessary, to prevent failure in grip areas.

Figure 5:
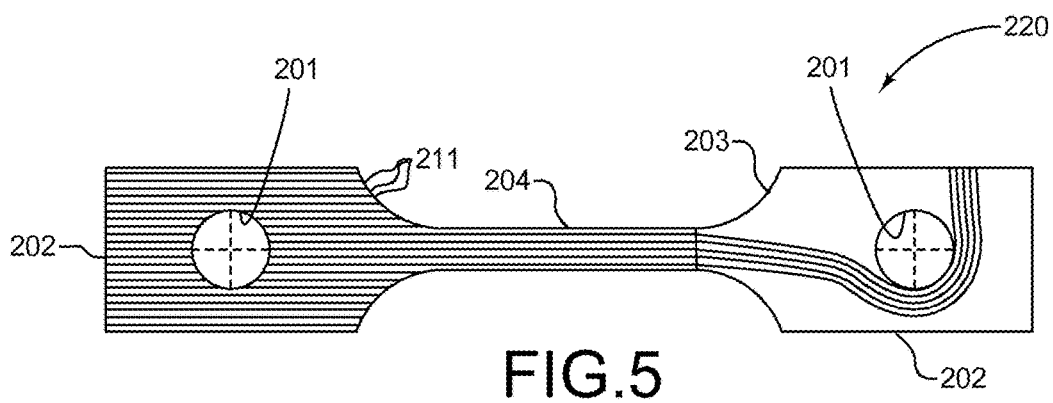
FIG. 5 is a plan view of one layer of a composite layup structure having the shape of the test specimen shown in FIG. 4, but with reinforcing fibers, and particularly illustrating the arrangement of the reinforcing fibers so they extend around one of the holes in the grip portion and so that the fibers are not cut when the hole is made. The left side of FIG. 5 illustrates the cutting of longitudinally arranged fibers when the hole is made.
Figure 6:
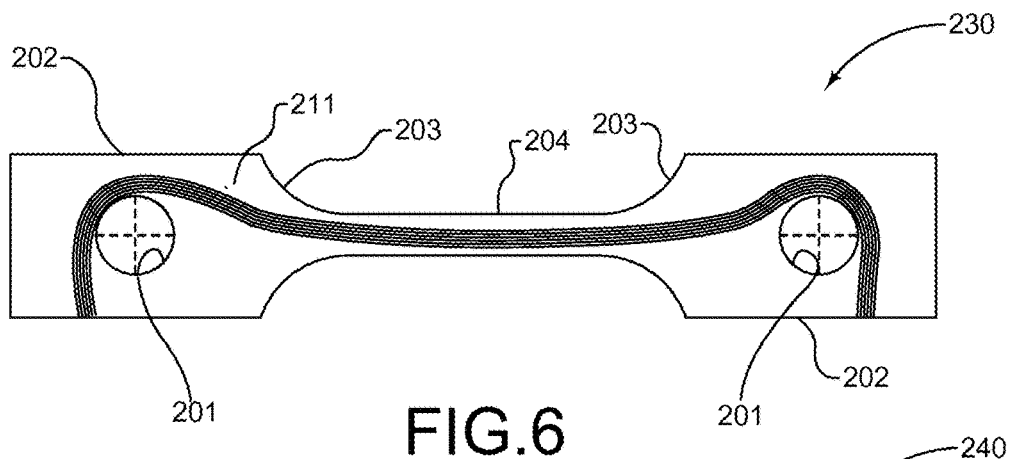
FIG. 6 is another plan view of at least one layer of a composite layup structure, wherein the layer includes reinforcing fibers and the reinforcing fibers are arranged to extend around the holes disposed in the grip portions so that the fibers are not cut once holes are made.

Suitable test specimens may also be fabricated from composite layup structures having a plurality of layers or plies, at least some of which include reinforcing fibers. Turning to FIGS. 5-13, various layers 220, 230, 240, 250, 260, 270, 280, 290, 300 of possible composite layup structures are shown. FIG. 5 illustrates a problem created when holes 201 are drilled or punched through grip regions 202 through which reinforcing fibers 211 pass. Specifically, on the left side of FIG. 5, the creation of the hole 201 results in a number of the fibers 211 being cut or broken, resulting in a high amount of shear transfer required to transfer the load around the hole 201. Referring to the hole 201 shown at the left in FIG. 5, it is extremely likely that a tensile specimen fabricated from the layer 220 would fail near the hole 201 shown at the left in FIG. 5. As a solution to this problem, the fibers 211 are rearranged on the right side of the layer 220 shown in FIG. 5. Specifically, the fibers 211 are arranged so they wrap or extend around the hole 201 shown at the right in FIG. 5 (see also FIGS. 6, 9-10). The fibers 211 that extend around the hole 201 shown at the right in FIG. 5 are able to take the bearing load when accommodated by symmetric fibers, as shown in FIG. 6. The layer 230 shown in FIG. 6 would complement a layer such as that shown at 220 in FIG. 5 because the fibers 211 wrap around the holes 201 in opposite directions and therefore the layers 220, 230 could be used as alternating layers in a composite layup structure.

Figure 7:
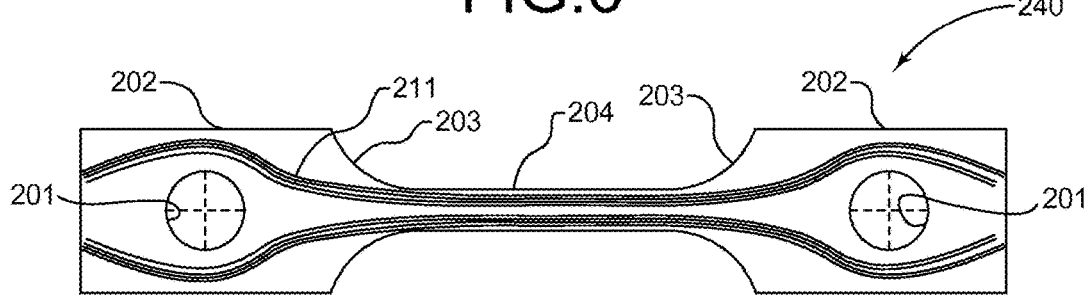
FIG. 7 is another plan view of at least one layer of a composite layup structure, wherein the layer includes reinforcing fibers that are arranged to avoid the areas where the holes are subsequently made, thereby avoiding cutting of the reinforcing fibers that extend through the gauge region.
Figure 8:
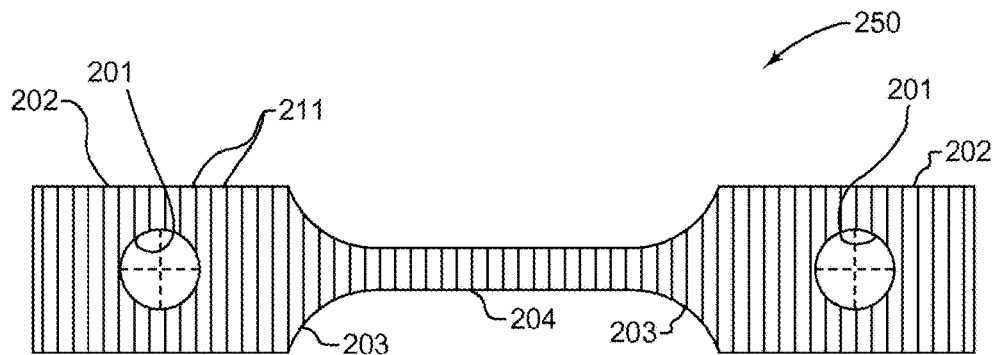
FIG. 8 is another plan view of at least one layer of a composite layup structure, when the layer includes reinforcing fibers that are disposed transversely to the longitudinal direction of the layer.
Figure 9:
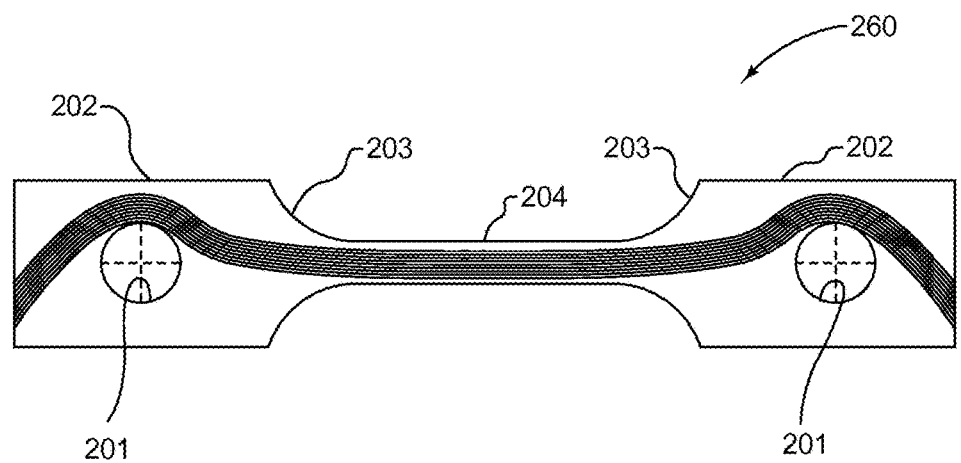
FIG. 9 is another plan view of at least one layer of a composite layup structure, wherein the layer includes reinforcing fibers that extend around both holes in the grip portions of the layer and proceed towards a corner of the respective grip portion at an angle of about 45° with respect to a longitudinal axis that proceeds through the gauge region.
Figure 10:
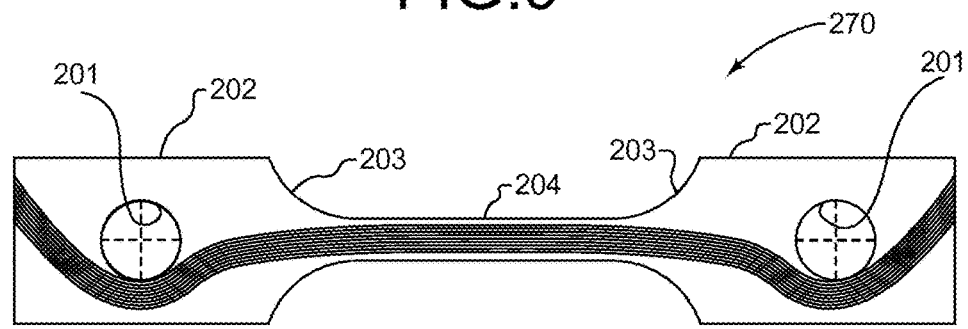
FIG. 10 is another plan view of at least one layer of a composite layup structure that is similar to FIG. 9 but with an opposite configuration and therefore portions of the fibers extending through the grip portions and past the holes would be disposed transversely to the corresponding fiber portions shown in FIG. 9.
Figure 11:
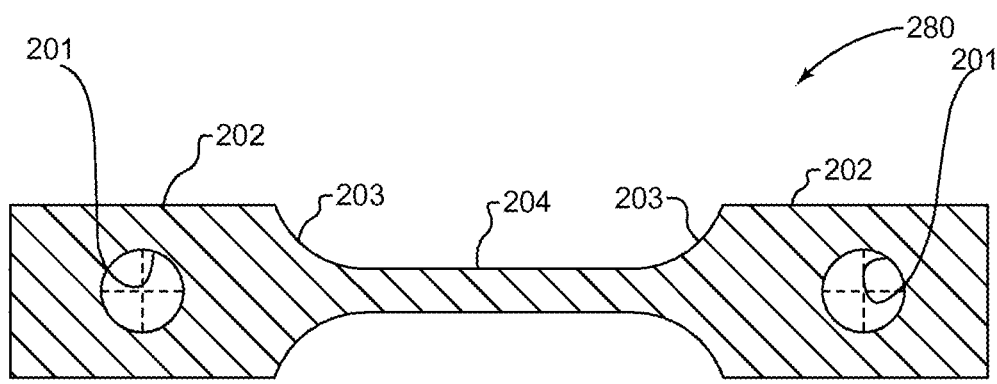
FIG. 11 is another plan view of at least one layer of a composite layup structure, wherein the layer includes reinforcing fibers disposed at about a 45° angle with respect to a longitudinal axis passing through the gauge region.
Figure 12:
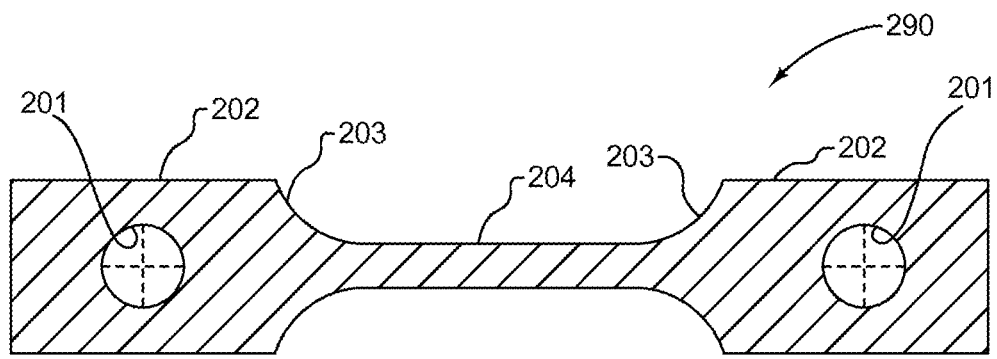
FIG. 12 is another plan view of at least one layer of a composite layup structure, wherein the layer includes reinforcing fibers disposed at about a 45° angle with respect to a longitudinal axis passing through the gauge region, but transversely with respect to the fibers illustrated in FIG. 11.
Figure 13:
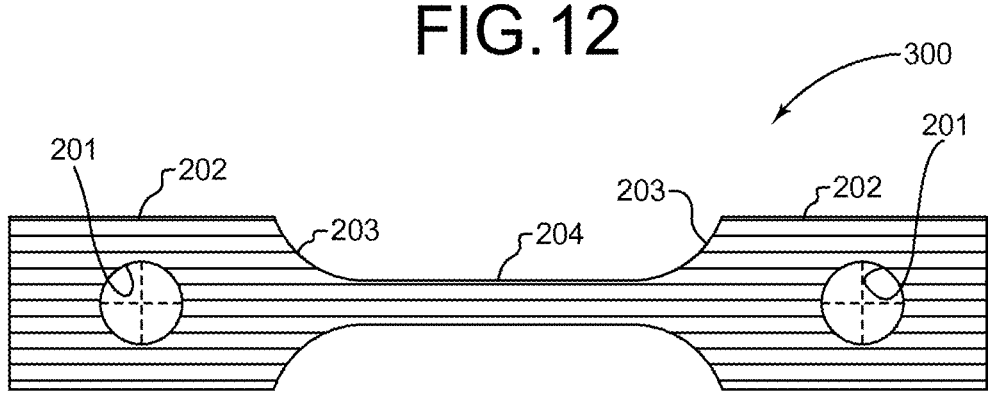
FIG. 13 is another plan view of at least one layer of a composite layup structure, when the layer includes reinforcing fibers that extend longitudinally through the layer.

Similarly, the layers 240, 250 of FIGS. 7-8 respectively could complement each other if used as alternating plies in a composite layup structure as the layer 240 includes fibers 211 that extend longitudinally through the layer 240 and around the holes 201 in a Y arrangement. To complement the arrangement shown in the layer 240 of FIG. 7, fibers 211 that extend transversely to a longitudinal axis of the layer 250 are shown in FIG. 8. Thus, the fibers 211 of FIG. 8 extend substantially transversely to the fibers 211 of FIG. 7 and therefore the layers 240 and 250, when used as alternating layers in a composite layup structure, are able to complement each other and provide resistance to tearing at the bearing hole. Similarly, such a complementary, transverse relationship may be created by using the layers 260, 270 of FIGS. 9-10 in an alternating fashion. Another example of suitable alternating plies or layers is illustrated by the layers 280 and 290 of FIGS. 11-12 (±45°) as well as the layers 250 and 300 of FIGS. 8 and 13 (0.90°).

Thus, composite materials may be used as a substrate that is plated to form a lightweight but strong metallic part, such as a case, duct, housing, enclosure, panel, etc. Other metallic parts that can be fabricated from a shaped composite article or substrate that is plated with one or more metallic layers will be apparent to those skilled in the art.

Brush Plating for Repair of Plated Polymer Parts

The interfacial strength between the plating and polymer materials in a plated polymeric structure is the weak point and can be structurally limiting. When plating does not adhere to the polymeric substrate, due to activation problems, contamination, etc., or if the plating gets nicked, dented or scratched, it can be cost effective to repair the plated polymer component rather than scrapping it. To repair a plated polymer part or component, brush plating or brush electroplating may be employed.

In brush plating, localized areas or entire parts may be plated using a brush saturated with plating solution. The brush is typically a stainless steel or graphite body wrapped with a cloth material that both holds the plating solution and prevents direct contact with the part being plated. The brush connects to the positive side of a low voltage direct-current power source, and the item to be plated connected to the negative side. Solution is pumped through a plating wand to maintain a fresh supply of solution. The operator dips the brush in the plating solution and then applies the brush to the part, moving the brush continually to get an even distribution of the plating solution over the part. Brush electroplating has several advantages over tank plating, including portability and ability to plate parts that for some reason cannot be tank plated, such as very large parts. Brush electroplating involves little or no masking requirements and uses comparatively little plating solution. Disadvantages compared to tank plating can include greater operator involvement (tank plating can frequently be done with minimal attention), and the inability to achieve as great a plate thickness.

The mechanics of brush plating are relatively straightforward. A 110-volt AC power pack converts the voltage into DC current. A ground cable carrying a negative charge is connected to the article being plated, which renders the article as the cathode. A second cable is carrying a positive charge is connected to the brush or plating tool, which makes it the anode. The brush is wrapped in an absorbent material, which holds the plating solution between the anode (the brush) and the cathode (the article being plated). Electrical current travels from the brush, through the plating solution to the work area on the article being plated. Plating occurs only when and where the brush contacts the article. Little to no heat is generated throughout the plating process, therefore no internal stress or heat distortions are imparted to the article. The metallic layer is dense, hard, corrosion resistant and metallurgically sound.

A closely related process is brush electroplating. In brush electroplating, an article is also plated using a brush saturated with a plating solution. The brush is typically made of stainless steel and wrapped with a cloth material that holds the plating solution. The cloth as prevents direct contact between the stainless steel brush and the item being plated. The brush is connected to the positive side of a low voltage DC power source, and the article to be plated is connected to the negative side of the DC power source. After the brush is dipped in the plating solution, the brush is moved continually over the surface of the article to achieve an even distribution of the plating material to form a metallic layer. The brush as the anode, typically does not contribute any plating material.

Repairing damaged areas of plated polymer components and restoring full membrane strength of the plating using an economical brush plating process can mean cost savings, extended service life and improved physical appearance of the part.

Use of Brush Plating in the Balancing of Polymer Components and Plated Polymer Components Rotating components, such as tires, spinners and fan platforms, typically must be balanced. The balancing of a rotating component is often achieved by attaching a metal weight or bonding one or more weights to an interior of the component. Currently, one balance method is to use metal powder filled resins as balance "putty" and this putty may be bonded to the component. Disclosed herein are brush plating and brush electroplating techniques, which can be used to balance rotating components.

In brush plating, localized areas or entire parts may be plated using a brush saturated with plating solution. The brush is typically a stainless steel or graphite body wrapped with a cloth material that both holds the plating solution and prevents direct contact with the part being plated. The brush connects to the positive side of a low voltage direct-current power source, and the item to be plated connected to the negative side. Solution is pumped through a plating wand to maintain a fresh supply of solution. The operator dips the brush in the plating solution and then applies the brush to the part, moving the brush continually to get an even distribution of the plating solution over the part. Brush electroplating has several advantages over tank plating, including portability and ability to plate parts that for some reason cannot be tank plated, such as very large parts. Brush electroplating involves little or no masking requirements and uses comparatively little plating solution. Disadvantages compared to tank plating can include greater operator involvement (tank plating can frequently be done with minimal attention), and the inability to achieve as great a plate thickness.

The mechanics of brush plating are relatively straightforward. A 110-volt AC power pack converts the voltage into DC current. A ground cable carrying a negative charge is connected to the article being plated, which renders the article as the cathode. A second cable is carrying a positive charge is connected to the brush or plating tool, which makes it the anode. The brush is wrapped in an absorbent material, which holds the plating solution between the anode (the brush) and the cathode (the article being plated). Electrical current travels from the brush, through the plating solution to the work area on the article being plated. Plating occurs only when and where the brush contacts the article. Little to no heat is generated throughout the plating process, therefore no internal stress or heat distortions are imparted to the article. The metallic layer is dense, hard, corrosion resistant and metallurgically sound.

A closely related process is brush electroplating. In brush electroplating, an article is also plated using a brush saturated with a plating solution. The brush is typically made of stainless steel and wrapped with a cloth material that holds the plating solution. The cloth as prevents direct contact between the stainless steel brush and the item being plated. The brush is connected to the positive side of a low voltage DC power source, and the article to be plated is connected to the negative side of the DC power source. After the brush is dipped in the plating solution, the brush is moved continually over the surface of the article to achieve an even distribution of the plating material to form a metallic layer. The brush as the anode, typically does not contribute any plating material.

Thus, brush plating and/or brush electroplating may be used to selectively plate a component, while it is rotating, or in-situ. Brush plating and brush electroplating are performed much faster than conventional plating (about 10 mils per hour) and provides a higher-strength bond than an adhesive. The exact thickness of the plating required may depend on the density of the weight, and the proper density the weight and the mass of the weight required to balance the component can be determined prior to the brush plating.

An alternate method may be to fix a balance weight (metal, polymer, or any other material) in place on the rotatable component, and use in-situ brushed plating to permanently entrap the weight onto the component. The plating layer(s) may extend beyond the weight, entrapping the weight against the rotating component, while providing superior bonding of the weight to the component as the plating layer is bonded to both the weight and the substrate.

INDUSTRIAL APPLICABILITY

Various means for forming lightweight metal parts or hollow metal parts are disclosed. A polymer suitable for being plated is selected and formed into an article of a desired shape by injection-molding, blow-molding, compression-molding or additive manufacturing. The outer surface of the formed article may be prepared for receiving a catalyst via etching, abrading, reactive ion etching, deposition of a conductive material, etc. Depending upon the process utilized to prepare the polymeric substrate, the outer surface may need to be rinsed or subjected to a neutralizing solution. Then, the outer surface may be activated with a catalyst such as palladium. Optionally, an accelerator may be applied before an electroless plating of a first layer of metal onto the outer surface of the formed polymers is carried out to form a metallic structure. The first layer of metal is typically electroless nickel. Then, if electroless nickel is not the desired material for the finished product or if the desired thickness has not been reached, an optional second layer of metal may be electrolytically plated onto the structure wherein the second layer of metal may typically be copper. If the desired thickness has not been reached or a different metal is desired for the final structure, one or more optional metallic layers may be applied to the structure. The additional metallic layer(s) may be applied via electroplating, electroless plating, electroforming, thermal spray coating, plasma vapor deposition, chemical vapor deposition, cold spraying, or, to the extent applicable, combinations thereof.

The polymer may be evacuated from the formed structure using an opening integral to the structure or through a hole formed in the structure. The polymer may be evacuated by etching, melting, applications of strong base and/or stripping agents or another suitable process as will be apparent to those skilled in the art. The hole(s) may then be plugged and additional metallic layers may be deposited onto the structure. A heat treatment may be carried out which may alloy or produce certain desired metallurgical reactions (these reactions include, but are not limited to the formation of inter-metal phases, solution treating, and precipitation hardening) in the layer(s). This heat treatment may be carried out in the form of transient liquid phase bonding, brazing, diffusion bonding, or other processes that will be apparent to those skilled in the art.

What is claimed is:

1. A method for balancing a rotatable component, the method comprising:
   rotating the component; and
   selectively plating the rotating component to deposit a metal layer onto the component until the component is balanced, wherein the plating is selected from the group consisting of brush plating and brush electroplating.

2. The method of claim 1 wherein the brush plating comprises a brush saturated with plating solution.

3. The method of claim 2 wherein the brush is selected from the group consisting of stainless steel or graphite.

4. The method of claim 3 wherein the brush is further wrapped with a cloth material that holds the plating solution and prevents direct contact with the component being plated.

5. The method of claim 1 wherein the brush electroplating comprises a brush saturated with plating solution.

6. The method of claim 5 wherein the brush is selected from the group consisting of stainless steel or graphite.

7. The method of claim 6 wherein the brush is further wrapped with a cloth material that holds the plating solution and prevents direct contact with the component being plated.

8. A method for balancing a rotatable component, the method comprising:
   attaching a balancing weight to the rotatable component;
   rotating the component; and
   selectively plating the rotating component and the balancing weight to deposit a metal layer onto the balancing weight and the component until the component is balanced, wherein the plating is selected from the group consisting of brush plating and brush electroplating.

9. The method of claim 8 wherein the brush plating comprises a brush saturated with plating solution.

10. The method of claim 9 wherein the brush is selected from the group consisting of stainless steel or graphite.

11. The method of claim 10 wherein the brush is further wrapped with a cloth material that holds the plating solution and prevents direct contact with the component being plated.

12. The method of claim 8 wherein the brush electroplating comprises a brush saturated with plating solution.

13. The method of claim 9 wherein the brush is selected from the group consisting of stainless steel or graphite.

14. The method of claim 10 wherein the brush is further wrapped with a cloth material that holds the plating solution and prevents direct contact with the part being plated.

15. The method of claim 8 wherein the balancing weight is selected from the group consisting of metals, metal powder filled resins and polymers.

16. A method for balancing a rotatable fan assembly, the method comprising:
   attaching a balancing weight to the fan assembly;
   rotating the fan assembly; and
   plating the fan assembly and the balancing weight to deposit a metal layer onto the balancing weight and fan assembly until the fan assembly is balanced, wherein the plating is selected from the group consisting of brush plating and brush electroplating.

17. The method of claim 16 wherein the balancing weight is selected from the group consisting of metals, metal powder filled resins and polymers.

* * * * *